United States Patent [19]

Greenwood

[11] 4,335,205

[45] Jun. 15, 1982

[54] LOW PROTEIN DEGRADATION PRODUCT BASAL MEDIUM FOR IDENTIFICATION OF NON-FERMENTATIVE GRAM-NEGATIVE BACILLI AND OTHER MICROORGANISMS

[76] Inventor: James R. Greenwood, 1275 Barry Ave., Apt. #4, Los Angeles, Calif. 90025

[21] Appl. No.: 27,843

[22] Filed: Apr. 6, 1979

[51] Int. Cl.³ .............................................. C12Q 1/04
[52] U.S. Cl. ...................................... 435/34; 435/36; 435/37; 435/38; 435/253; 435/301; 435/875
[58] Field of Search ........................ 435/29, 34, 36, 37, 435/38, 243, 244, 253, 299, 300, 301, 874, 875

[56] References Cited

U.S. PATENT DOCUMENTS 3,399,115  8/1968  Sellers, Jr. ............................. 435/34
4,048,016  9/1977  Otto ...................................... 435/34

OTHER PUBLICATIONS

Edwin Lennette et al., Editors, Manual of Clinical Microbiology, 2nd ed. American Society for Microbiology, pp. 252–255, 1974.
Difro Manual, 9th Ed., Difro Laboratories, p. 265, 1953.

Primary Examiner—Robert J. Warden
Attorney, Agent, or Firm—Harlan P. Huebner

[57] ABSTRACT

A single basal growth medium for receiving various substrates for the purpose of rapid identification of any species of non-fermentative Gram-negative bacilli (NFB), wherein the medium is low in organic nitrogen but is supplemented with inorganic nitrogen from an ammonium ion source to enhance NFB growth. The medium also serves to identify members of the family Enterobacteriaceae, cytochrome oxidase positive fermenters, Gram-positive bacilli, Gram-positive cocci, and anaerobes.

11 Claims, No Drawings

LOW PROTEIN DEGRADATION PRODUCT BASAL MEDIUM FOR IDENTIFICATION OF NON-FERMENTATIVE GRAM-NEGATIVE BACILLI AND OTHER MICROORGANISMS

BACKGROUND OF THE INVENTION

In the prior art many media have been developed for the identification of bacteria but most prior art media have had limited capabilities. Some, for example, have been used for determining only a single biochemical reaction of an unknown microorganism. Others have been compounded to identify only fermentative or non-fermentative bacteria.

A primary problem in the prior art media has been an inordinate incubation time for positive reactions. Prolonged incubation time for bacterial speciation is particularly hazardous in cases of nosocomial infections or post-operative wound infections.

*Pseudomonas aeruginosa, Acinetobacter anitratus, P. maltophilia,* and many other NFB are becoming increasingly recognized as important causes of infection and therefore it is mandatory that they be rapidly isolated and identified. While most commercially available isolation media are applicable for NFB, identification methodology for these organism has been inadequate.

Two known prior art media have been developed for the identification of NFB. One is disclosed in U.S. Pat. No. 3,399,115 to Sellers. This medium is capable of identifying only five species of NFB. This medium includes a large amount of organic nitrogen. In general a large amount of organic nitrogen tends to cause additional alkaline byproducts of metabolism so that positive reactions are significantly delayed and in addition unreliable results are obtained. The Sellers patent does suggest the use of inorganic nitrogen.

The second medium is disclosed in U.S. Pat. No. 4,048,016 to Otto. The Otto disclosure is essentially that of a non-growth or buffered substrate medium. For inoculation it requires a heavy inoculum, that is, an inoculum of about $10^{11}$ organisms per milliliter. This is obtained by harvesting numerous (50 to 100) bacterial colonies and requires an additional time of 24 hours for NFB identification.

SUMMARY OF THE INVENTION

Although there are over thirty species of clinically encountered NFB, three of the species account for more than 90% of the clinical isolates. The three common species, *Pseudomonas aeruginosa, Pseudomonas maltophilia* and *Acinetobacter anitratus,* and the other twenty-seven species are efficiently and rapidly identified by the basal growth medium according to the invention.

The success of the present medium is due to the discovery of the use of a small amount of organic nitrogen supplemented with inorganic nitrogen in the form of an ammonium ion source. It was known that low organic nitrogen does not support adequate growth of NFB but it was surprisingly discovered that the addition of inorganic nitrogen, in the form of an ammonium ion, greatly enhanced NFB growth without producing the additional alkaline byproducts of metabolism that occur with the prior art use of organic nitrogen in amounts sufficient to permit NFB growth. The same results were surprisingly obtained in the identification of other microorganisms to be described.

The limited low organic nitrogen is necessary to show the rapid attack of carbohydrates and to show the attack of organic salts and amides without any false positive reactions due to the extremely proteolytic nature of most NFB. The ammonium ion source, however, has been found to be an ideal supplement to provide sufficient NFB growth for identification.

Accordingly, it is an object of the present invention to provide an improved basal medium to which substrates may be added whereby virtually all species of NFB and other microorganisms can be identified.

It is another object of the invention to provide a basal medium, as described in the preceding paragraph, containing a relatively low amount of organic nitrogen in the form of a low protein degradation product, supplemented with inorganic nitrogen in the form of an ammonium ion.

It is still another object of the invention to provide a basal medium, as described in the preceding paragraphs, by which the reaction time of identification of particular NFB and other microorganisms is reduced to a maximum of 24 hours.

It is a further object of the invention to provide a basal medium, as described in the preceding paragraphs, in which a relatively light inoculum may be used to accomplish identification of NFB. That is, only one bacterial colony is needed to inoculate from 25 to 30 substrates in a miniaturized multi-compartmented container. That the invention permits the use of the relatively light inoculum saves 24 hours of identification time over the prior art.

It is a still further object of the invention to provide a basal medium, as described in the preceding paragraphs, which when combined with an appropriate substrate may be used as a liquid, semi-solid or solid. Agar is used as a gelling agent to reduce the fluidity.

It is another object of the invention to provide a basal medium, as described in the preceding paragraphs, by which bacteria other than NFB can be identified. For example, Enterobacteriaceae, cytochrome oxidase positive fermenters, Gram-positive cocci, Gram-positive bacilli, and anaerobes can also be identified with the use of this basal medium and the proper selection of known substrates.

Further objects and advantages of the invention may be brought out in the following part of the specification wherein small details have been described for the competence of disclosure, without intending to limit the scope of the invention which is set forth in the appended claims.

DESCRIPTION OF THE PREFERRED EMBODIMENTS

The basal growth medium of the invention is comprised of organic nitrogen in the form of a protein degradation product, inorganic nitrogen in the form of an ammonium salt, any potassium salt, any magnesium salt, yeast extract, an indicator and water. The organic nitrogen may be peptones in general, protein hydrolysate, trypticase, casamino acids, Poly peptone, pancrearic digest of casein. The ammonium salts may be ammonium chloride, ammonium sulfate, ammonium hypophosphate, ammonium hypophosphite, or ammonium orthophosphate, for example.

The indicator may be brom cresol purple, brom thymol blue or phenol red.

A suitable basal medium is comprised of the following:

| | |
|---|---|
| One of the above ammonium salts | 0.5 to 1.5 gm. |
| Any potassium salt | 0.1 to 0.3 gm. |
| Any magnesium salt | 0.1 to 0.3 gm. |
| Yeast extract | 0.2 to 1.0 gm. |
| One of the above organic nitrogen compounds | 0.2 to 1.0 gm. |
| Agar | 0.00 to 60.0 gm. |
| One of the above indicators | 0.002 to 0.060 gm. |
| Water to make | 1000 ml. |

It has been found that amounts in excess of the maximum of the above ranges are of no benefit.

To the above basal medium, substrates ranging from 2.0 to 25.0 grams are added, and the pH adjusted depending on the type of indicator and substrate used. The pH range preferably is varied between 6.2 and 7.8. For example, a substrate to be acidified is adjusted to pH 7.0±0.1 when phenol red is used. For brom cresol purple the pH is adjusted to 7.5±0.2. Substrates that are alkalinized are adjusted to pH 6.5±0.2 when phenol red is used and pH 7.0±0.2 when brom cresol purple is the indicator.

Examples of subsrates that can be alkalinized in the above medium to identify NFB are salts of dicarboxylic acids; hydroxy acids, e.g. tartrate; sugar derivative, e.g., saccharates; ring amino acids, e.g., phenylalanine; amides, e.g., glutamine; and certain nitrogen compounds including allantoin and asparagine. It was also surprisingly found that the hyrolysis of gelatin was accomplished by the alkalinization of it as a substrate in the basal medium.

When the basal medium is used in the alkalinization of the above organic salt and amide substrates, 0.1% by weight of dextrose is added. The added dextrose balances the slight alkaline shift caused by the bacterial attack of the organic nitrogen and yeast extract in medium. A positive identification of an NFB is made when alkalinization occurs as shown by the indicator change in a particular substrate.

Examples of substrates that can be acidified in the above medium to identify NFB are poly-alcohols, e.g., glycol, M-inositol, and D-Mannitol; disaccharides, e.g., cellobiose and lactose; pentoses, e.g., L-arabinose, D-xylose, D-ribose and rhamnose; heptoses, e.g., D-fructose; and hextoses, e.g., glucose. A positive identification of an NFB is made when acidification occurs as shown by the indicator change in a particular substrate.

The basal medium of this invention may be of three general consistencies. One is in the form of a liquid to make a broth, accomplished by not including agar. The other two are semisolid and solid. These are achieved by adding agar: for the semisolid 1.0 to 1.3% by weight and for the solid above 1.4% by weight.

The following example is presented as a typical basal medium of the invention:

| | |
|---|---|
| Ammonium phosphate | 1.0 gm. |
| Potassium chloride | 0.2 gm. |
| Magnesium sulfate | 0.2 gm. |
| Yeast extract | 0.5 gm. |
| Casitone | 0.5 gm. |
| Agar | 15.0 gm. |
| Phenol red | 0.020 gm. |
| Water to make | 1000 ml. |

To this basal medium the appropriate substrates may be added so as to, in an appropriate test apparatus, identify all species of NFB, and in particular the three common species.

EXAMPLE 1

A series of agar slants of the above basal medium were prepared with the following substrates: citrate, dextrose, L-arabinose, lactose, D-mannitol, acetamide, tartrate, gelatin and starch.

To make the agar slants each of the above compounds was weighed and added to one liter of cold distilled water. The pH was adjusted to the proper starting point for the substrate, and the ingredients were steamed to melt the agar. The medium was dispensed into test tubes and autoclaved for 15 minutes. After autoclaving the medium was cooled to approximately 50° C. and a filter sterilized substrate was added to provide a final concentration of 1% by weight of the basal medium. The completed combinations were then cooled in a slanted position and solidifed.

Each of the slants was inoculated with a single 24 hour colony of an NFB and then incubated for 24 hours at 35° C. in an air incubator. After 24 hours of incubation the reactions were read in the tubes and the results tabulated in Table 1. From the results it can be seen that most NFB produced positive reactions in 24 hours.

TABLE 1

| Test | Non-fermentative bacilli (NFB) | | | | | |
|---|---|---|---|---|---|---|
| | P. cepacia | P. aeruginosa | P. maltophilia | P. putida | P. acidovorans | A. odorans |
| *Acetamide | − | + | − | − | + | + |
| *Citrate | + | + | + | + | − | + |
| *Gelatin | +$^w$ | − | + | − | − | − |
| *Tartrate | + | − | − | + | + | + |
| **Dextrose | + | + | + | + | − | − |
| **L-Arabinose | + | + | − | − | − | − |
| **D-Mannitol | + | + | − | − | + | − |
| **Starch | − | − | − | − | − | − |
| **Lactose | + | − | − | − | − | − |

+ = positive within 24 hours; +$^w$ = weak positive within 24 hours; − = negative through 72 hours of incubation.
*started with acid pH, when positive became alkaline.
**started with alkaline pH, when positive became acid.

EXAMPLE 2

Table 2 is a listing of the identification results of 521 NFB identified with the basal medium of the invention. The medium and particular substrates were inoculated and incubated substantially as outlined above in Example 1. From the results in Table 2, it can be seen that virtually 100% of the three most common species of NFB were identified within 24 hours.

Other basal medium substrates were added after 24 hours to effect the identification of the less frequently encountered NFB, such as *Alcaligenes odorans*, *P. acidovorans*, and *P. putida*. The less commonly encountered NFB could also be identified by initial inoculation of additional substrates.

TABLE 2
521 NFB IDENTIFIED WITH LOW PROTEIN DEGRADATION PRODUCT SYSTEM

| ORGANISM | % OF TOTAL | CUMULATIVE % IDENTIFIED WITHIN | | |
|---|---|---|---|---|
| | | 24h | 48h | More than or equal to 72h |
| *Pseudomonas aeruginosa* | | | | |
| Nonpigmented | 9 | 88 | 100 | |
| Pigmented | 65 | 98 | 100 | |
| *P. maltophilia* | 7 | 100 | | |
| *Acinetobacter anitratus* | 7 | 100 | | |
| *A. lwoffi* | 3 | 100 | | |
| *Flavobacterium* IIb | 1 | 57 | 100 | |
| *P. stutzeri* | 1 | 0 | 71 | 100 |
| *Alcaligenes odorans* | 1 | 0 | 100 | |
| *P. acidovorans* | 1 | 0 | 75 | 100 |
| *P. cepacia* | 1 | 0 | 75 | 100 |
| *Moraxella* sp. | 1 | 0 | 100 | |
| *P. putrefaciens* Less than | 1 | 100 | | |
| *P. putida* Less than | 1 | 0 | 100 | |
| *P. denitrificans* Less than | 1 | 0 | 0 | 100 |
| *P. pseudoalcaligenes* Less than | 1 | 0 | 100 | |
| *P. diminuta* Less than | 1 | 0 | 100 | |
| *P. vesicularis* Less than | 1 | 0 | 0 | 100 |
| *Kingella kingae* Less than | 1 | 0 | 100 | |
| *Flavobacterium* IIa Less than | 1 | 0 | 100 | |
| *Bordetella bronchiseptica* Less than | 1 | 0 | 100 | |
| CDC IIk Less than | 1 | 0 | 100 | |
| K 988 Less than | 1 | 0 | 0 | 100 |

EXAMPLE 3

Table 3 is a representative listing of additional bacteria tested on the basal medium described above. This group of bacteria includes members of the family Enterobacteriaceae and cytochrome oxidase positive fermenters. It can be seen that these test organisms also give position reactions in 24 hours. Similar rapid reactions have also been noted with Gram-positive bacilli, Gram-positive cocci, and anaerobes.

TABLE 3

| | Bacteria | | | | |
|---|---|---|---|---|---|
| Test | *Klebsiella pneumoniae* | *Enterobacter agglomerans* | *Proteus morganii* | *Serratia marcescens* | *Pasteurella multocida* |
| **ARABINOSE | + | + | − | + | − |
| **DEXTROSE | + | + | + | + | +ʷ |
| **SUCROSE | + | + | − | + | +ʷ |
| **LACTOSE | + | − | − | − | − |
| **INOSITOL | + | + | − | + | − |
| *GELATIN | − | − | − | + | − |
| *UREA | + | − | + | − | − |
| *GLUTAMINE | + | − | − | + | − |

+ = positive within 24 hours; +ʷ = weak positive within 24 hours; − = negative through 72 hours of incubation.
*started with acid pH, when positive became alkaline.
**started with alkaline pH, when positive became acid.

A kit for use in identifying all NFB will contain a multiple array of the basal media in poured agar, dehydrated, or frozen form in a compartmented container or an identification strip. Each compartment will contain the basal medium. It will also contain a different selected substrate and the proper indicator, as known in the art. Additional tests, such as Beta-Galactosidase, hydrogen sulfide production, Voges-Proskauer, ornithine decarboxylase, lysine decarboxylase, arginine decarboxylase, deoxyribonuclease, and other tests deemed necessary will be added to extend the range of organisms identified by such a kit identification system.

An example of the contents of such a kit is as follows:

| | | |
|---|---|---|
| One of the above ammonium salts | 0.05 to 0.15 | By weight % |
| Any potassium salt | 0.01 to 0.03 | " |
| Any magnesium salt | 0.01 to 0.03 | " |
| Yeast extract | 0.02 to 0.10 | " |
| One of the above organic nitrogen compounds | 0.02 to 0.10 | " |
| Agar | 0.00 to 6.0 | " |
| One of the above properly selected indicators | 0.0002 to 0.006 | " |
| Water, in proper percentages by weight, e.g. about 0.1 ml to 0.2 ml. | | |
| A selected substrate in each compartment for a particular NFB | 0.2 to 2.5 | By weight % |

The invention and its attendant advantages will be understood from the foregoing description and it will be apparent that various changes may be made in the form, construction and arrangements of the parts of the invention without departing from the spirit and scope thereof or sacrificing its material advantages, the arrangements hereinbefore described being merely by way of example. I do not wish to be restricted to the specific forms shown or uses mentioned except as defined in the accompanying claims, wherein various portions have been separated for clarity of reading and not for emphasis.

What I claim is:

1. A single low organic nitrogen basal growth medium for the relatively rapid identification of non-fermentative Gram-negative bacilli (NFB) and other microorganisms including the family Enterobacteriaceae, and cytochrome oxidase positive fermenters, comprising:

about 0.5 to about 1.5 gm. of an ammonium ion source,
about 0.1 to about 0.3 gm. of a potassium salt,
about 0.1 to about 0.3 gm. of a magnesium salt,
about 0.2 to about 1.0 gm. of yeast extract,
about 0.2 to about 1.0 gm. of an organic nitrogen source,
0.0 to about 60.0 gm. of agar, about 0.002 to about 0.060 gm. of an indicator selected from the group consisting of brom cresol purpose, brom thymol blue, and phenol red, and water sufficient to make 1000 ml.

2. The invention according to claim 1 in which:
said ammonium ion source is an ammonium salt.

3. The invention according to claim 1 in which:
the ammonium ion source is one selected from the group consisting of ammonium chloride, ammonium sulfate, ammonium hypophosphate, ammonium hypophosphite, and ammonium orthophosphate.

4. The invention according to claim 1 in which:
the organic nitrogen source is a protein degradation product.

5. The invention according to claim 1 in which:
the organic nitrogen source is one selected from the group consisting of protein hydrolysate, trypticase, casamino acids, Poly peptone, and pancrearic digest.

6. The invention according to claim 1 in which:
the organic nitrogen source is a peptone.

7. The invention according to claim 1 in which:
said medium has a pH range of about 6.2 to 7.8.

8. The invention according to claim 1 including:
a 2 to 25 gm. substrate alkalinized in said medium,
said substrate being one selected from the group consisting of salts of dicarboxylic acids, hydroxyacids, sugar derivatives, ring amino acids, amides, allantoin, asparagine, and gelatin,
the pH range being between 7 and 7.8, and
0.1% by weight dextrose.

9. The invention according to claim 1 including:
a 2 to 25 gm. substrate acidified in said medium,
said substrate being one selected from the group consisting of polyalcohols, disaccharides, pentoses, heptoses, and hexoses,
the pH range being between 6.2 and 7.

10. The invention according to claim 1 including:
a 2 to 25 gm. gelain used as a substrate in said medium to be hydrolyzed, and said hydrolosis being detected by an alkaline shift in said medium.

11. A kit for the relatively rapid identification of non-fermentative Gram-negative bacilli (NFB) and other microorganisms including the family Enterobacteriaceae, and cytochrome oxidase positive fermenter, comprising:
a multiple compartmented tray, each compartment containing a single low organic nitrogen basal growth medium including,
about 0.05 to about 0.15 by weight % of an ammonium ion source,
about 0.01 to about 0.03 by weight % of a potassium salt,
about 0.01 to about 0.03 by weight % of a magnesium salt,
about 0.02 to about 0.10 by weight % of yeast extract,
about 0.02 to about 0.10 by weight % of an organic nitrogen source,
0.00 to about 6.0 by weight % of agar,
a selected substrate for each compartment capable of being either acidified or alkalinized, and
in each compartment the selected indicator for the selected substrate capable of showing a positive reaction.

* * * * *